United States Patent
Simola et al.

(10) Patent No.: US 8,901,321 B2
(45) Date of Patent: Dec. 2, 2014

(54) PROCESS FOR RECOVERY OF MALEIC ANHYDRIDE BY USING ORGANIC SOLVENT

(75) Inventors: Flavio Simola, Monterotondo (IT); Salvatore Cassarino, Rome (IT); Antonio Iosco, Rome (IT)

(73) Assignee: Conser SpA, Rome (IT)

( * ) Notice: Subject to any disclaimer, the term of this patent is extended or adjusted under 35 U.S.C. 154(b) by 44 days.

(21) Appl. No.: 13/818,183

(22) PCT Filed: Dec. 13, 2010

(86) PCT No.: PCT/IT2010/000500
§ 371 (c)(1),
(2), (4) Date: Feb. 21, 2013

(87) PCT Pub. No.: WO2012/081043
PCT Pub. Date: Jun. 21, 2012

(65) Prior Publication Data
US 2013/0150594 A1    Jun. 13, 2013

(51) Int. Cl.
*C07D 307/36*  (2006.01)
*C07D 307/33*  (2006.01)
*C07D 307/60*  (2006.01)

(52) U.S. Cl.
CPC ............ *C07D 307/33* (2013.01); *C07D 307/60* (2013.01)
USPC ....................................................... 549/262

(58) Field of Classification Search
USPC ....................................................... 549/262
See application file for complete search history.

(56) References Cited

U.S. PATENT DOCUMENTS

| | | | |
|---|---|---|---|
| 2,574,644 | A | 11/1951 | Landau |
| 2,942,005 | A | 6/1960 | Brown |
| 3,818,680 | A | 6/1974 | Marquis |
| 3,948,623 | A | 4/1976 | Paradis et al. |
| 4,071,540 | A | 1/1978 | Marquis |
| 4,118,403 | A | 10/1978 | White |
| 4,314,946 | A | 2/1982 | Neri et al. |
| 5,631,387 | A | 5/1997 | Brown et al. |
| 6,093,835 | A | 7/2000 | Sawaki et al. |
| 6,921,830 | B2 | 7/2005 | Rallf et al. |
| 2009/0146301 | A1 | 6/2009 | Shimizu et al. |

FOREIGN PATENT DOCUMENTS

| | | |
|---|---|---|
| CN | 1062344 | 7/1992 |
| EP | 0 459 543 | 12/1991 |
| GB | 727828 | 4/1955 |
| GB | 763339 | 12/1956 |
| GB | 768551 | 2/1957 |
| JP | 5025154 | 2/1993 |
| WO | 2009121735 | 10/2009 |

OTHER PUBLICATIONS

International Search Report dated Jul. 27, 2011, corresponding to PCT/IT2010/000500.

*Primary Examiner* — T. Victor Oh
(74) *Attorney, Agent, or Firm* — Young & Thompson

(57) ABSTRACT

A process for the recovery of maleic anhydride from the gas produced by the catalytic oxidation of hydrocarbon, n-butane or benzene, is characterized by:
a) High efficiency in maleic anhydride recovery
b) Reduced formation of maleic acid and fumaric acid
c) Reduced maintenance, thanks to the prevented formation of solid deposits in the absorber and in other related equipment.

20 Claims, 3 Drawing Sheets

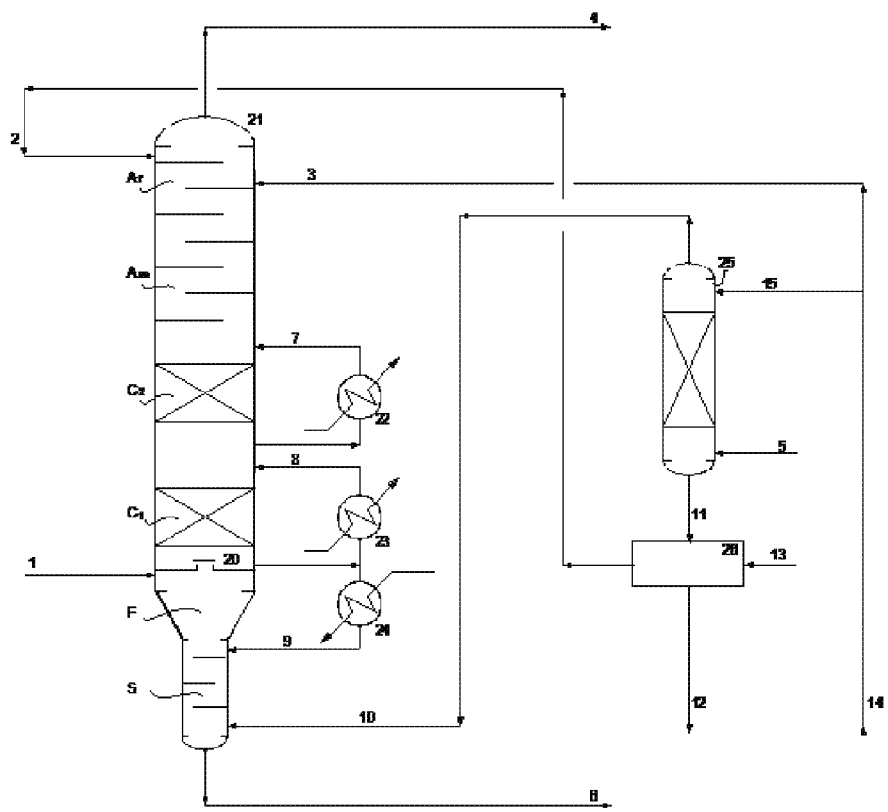

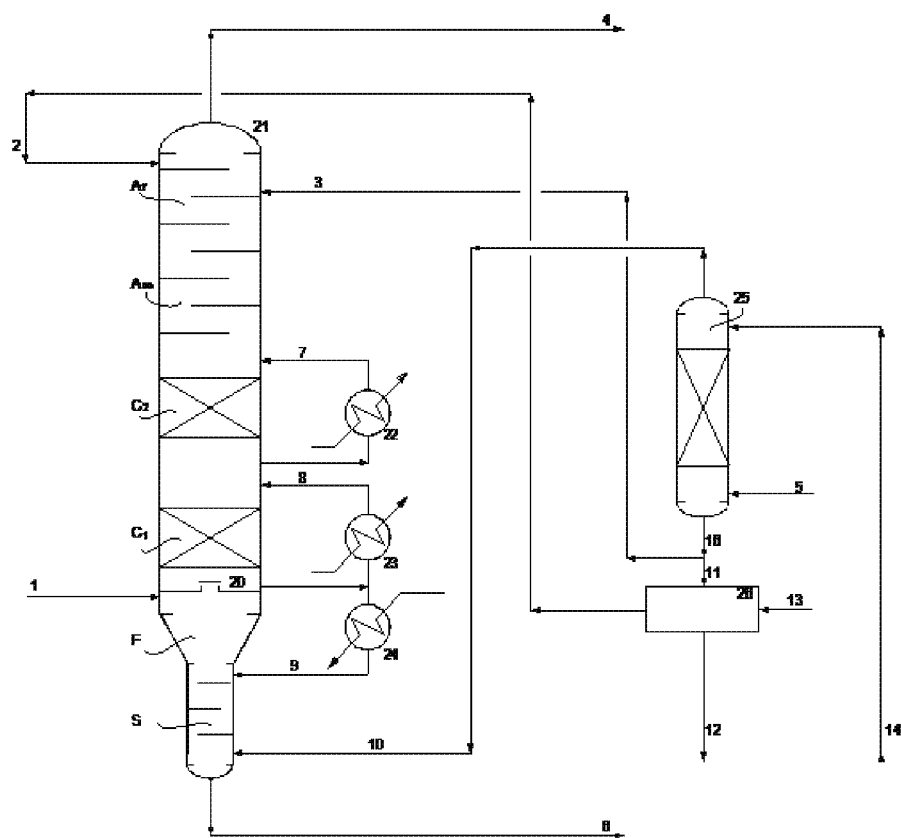

PROCESS FOR RECOVERY OF MALEIC ANHYDRIDE BY USING ORGANIC SOLVENT

FIELD OF DISCLOSURE

Embodiments disclosed herein relate generally to processes and equipment to recover maleic anhydride, produced by reacting a mixed gas containing molecular oxygen and an hydrocarbon, normally n-butane but also in some cases benzene, over a suitable catalyst. More specifically, embodiments relate to the recovery of the maleic anhydride contained in the reaction mixture gas by absorption in an organic solvent.

BACKGROUND OF THE INVENTION

Maleic Anhydride is an important raw material used in the manufacture of alkyd and unsaturated polyester resins and it is also a versatile intermediate for the chemical synthesis of butanediol and tetrahydrofuran. It is produced by partial oxidation of hydrocarbons, typically n-butane, over a vanadium-phosphorus-oxygen (VPO) catalyst contained in a tubular fixed bed or in a fluid bed reactor. In both types of reactor the substantial exothermic heat of reaction is removed with production of steam.

To reduce risks of explosivity, the effluent gas from the reaction typically contains only a small amount of maleic anhydride, i.e. from 0.6 to 1.2 percent by volume, together with other components, mainly nitrogen and residual oxygen, and with oxidation by-products, including carbon monoxide and dioxide, water, acetic acid, acrylic acid and other minor impurities.

In the conventional process, first used in the commercial applications, the maleic anhydride present with low concentration in the gaseous stream which leaves the oxidation reactor, after adequate cooling and in some cases partial condensation, is recovered by absorption in water, where the corresponding maleic acid is formed.

The conventional process has some major disadvantages, as for example, a low yields of recovery, owing to conversion of maleic acid to fumaric acid, an high energy consumption due to the hydration of all the maleic anhydride to maleic/fumaric acid and the subsequent dehydration to the anhydride form, a discontinuous steam demand, high manpower and maintenance requirements and the production of high amounts of waste water effluent.

An alternate process based on absorption of maleic anhydride with use of an organic solvent has been proposed.

U.S. Pat. No. 2,574,644 can be considered the first application mentioning the use of organic solvent, in particular dibutyl-phthalate (DBP), as a selective absorbent for maleic anhydride. The patent teaches that, thanks to the great solubility of maleic anhydride in, the solvent even at low temperature, the maleic anhydride can be recovered in a column using DBP as absorption medium even at moderate conditions of temperature and pressure. Subsequently the maleic anhydride is removed from the solvent by stripping under vacuum conditions and elevated temperature.

GB patent 727,828 and U.S. Pat. No. 2,942,005 refers to the use of dibutyl phthalate for simultaneous absorption, from a mixture gas containing maleic and phthalic anhydride, of both anhydrides which is followed by vacuum stripping and separation of the products by fractionation (GB 727,828) or by crystallization (U.S. Pat. No. 2,942,005).

GB patent 763,339 and GB patent 768,551 represent improvements of the organic solvent recovery system, where the rich solvent is subject to two subsequent stripping operations at controlled conditions of pressure and temperatures.

U.S. Pat. No. 3,818,680 discloses the use of an alkenyl or alkyl substituted succinic anhydride as absorption liquid in a column having a number of theoretical trays from 5 to 15 and operating at temperature between 65 to 125° C.

U.S. Pat. No. 3,891,680 describes the use of dialkyl phthalate esters, with lower vapor pressure than DBP, capable to prevent carryover loss of solvent out of the gas scrubbing column and out of the vacuum stripper. Preferred solvents are in the group of dihexyl ortophthalates.

U.S. Pat. No. 3,948,623 relates to a process for separating maleic anhydride from a gaseous mixture by absorption into an organic solvent fed to an absorption column, where the absorption heat is removed through the cooling of a recirculation solvent stream withdrawn from the lower part of the column and recycled in an intermediate section of the column.

U.S. Pat. No. 4,071,540 discloses the absorption of maleic anhydride by countercurrent contacting in a column, by using liquid solvent comprising polymethyl-benzophenones.

U.S. Pat. No. 4,118,403 represents a further application of phthalate esters, preferably dibutyl phthalate, as absorption liquid, in which the addition of some amount of phthalic anhydride permits a better control of the temperature at the bottom of the vacuum stripper, preventing an excessive decomposition of the dialkyl phthalate.

U.S. Pat. No. 4,314,946 refers to a process to recover maleic anhydride from reaction gases, by using a different group of organic solvents, specifically dialkyl esters of hexahydrophthalic acid, tetrahydrophthalic acid, methyl tetrahydrophthalic acid or methyl hexahydrophthalic acid.

EP patent 0459543 discloses an improved process to recover maleic anhydride with an organic solvent, specifically dibutyl phthalate, characterized by a reduced formation of maleic and fumaric acid due to a substantial removal of absorbed water from the enriched absorbent, by its stripping with a low humidity gas or by contacting it with a water absorbent of several types, including zeolites.

Chinese patent CN 1062344 refers to the use of different type of organic solvents, like phthalic dioctyl ester or dewaxed oil from refinery, to recover maleic anhydride from the catalytic oxidation of hydrocarbons.

Japanese patent JP5025154 moreover teaches the uses of another organic solvent consisting of tetrahydrothiophene 1,1-dioxide.

U.S. Pat. Nos. 5,631,387, 6,093,835 and 6,921,830 consider the removal of accumulated polymeric impurities and other contaminants from the recirculating solvent, the first by using water washing the second by using aqueous alkali solution and the third by distillation under sub-atmospheric pressure.

US patent application 2009/0143601 presents a process for preventing fumaric acid deposits in the preparation of maleic anhydride, in which the organic solvent, preferably a phthalate ester, is catalytically hydrogenated before being recycled to the absorption column.

Patent WO 2009/121735 also refers to a process for separating fumaric acid in the recirculating absorbent liquid, by means of a controlled precipitation as solid, by cooling or by evaporative concentration.

Most of the above mentioned patents applied in around 60 years do not concern the art of the absorption of the maleic anhydride into the organic solvent, which is supposed to be a very simple unit operation.

The few exceptions are as follows:

U.S. Pat. No. 3,948,623 explains that, in order to maintain a proper temperature profile in the absorption column, the cooling of the absorbent liquid sent to the top of the column, as was done in the prior art processes, is not sufficient. An additional heat removal is necessary: preferably the heat shall be removed by a cooled recycle loop of absorbent, withdrawing the liquid stream from the lower part of the column, cooling the stream and then recycling the resulting cooling absorbent to the column.

U.S. Pat. No. 4,314,946 briefly mentions under examples 1 and 3 that, in order to cool the reaction gas inside the absorber down to 60-65° C., which represents the right temperature of the gas leaving the absorber to have an efficient recovery of maleic anhydride, the absorption column shall be divided in two columns in series with a gas cooler in between. Of course it is a complex and expensive solution.

EP Patent 0459543, on the other hand, explains that the enriched liquid absorbent, containing not negligible amount of water, absorbed from the oxidation reaction gas, before to be sent to the vacuum stripping column, where the maleic anhydride is recovered from the rich liquid absorbent, should be subject to a drying step.

In spite of the lacking of interest of the patents literature in this subject, as a matter of fact the issues related to the absorption in an organic solvent, and more specifically in the dibutyl phthalate, which is the most important and common organic solvent in the industrial applications, are somewhat complex and some problems and drawbacks are present.

First the organic absorbent, although it could be a very selective solvent for maleic anhydride and rather hydrophobic (the mutual solubilities DBP-water are very low), all the same a moderate absorption of water occurs inside the absorber. The absorption of water in dibutylphthalate occurs in presence of maleic anhydride in liquid phase.

Under the above mentioned circumstances the absorption of water in DBP is not only controlled by the simple liquid-vapor equilibrium rules. It is know in the art that aqueous contact cause the conversion of part or most of the maleic anhydride to maleic acid. In this mechanism, an undesirable side reaction can also take place, consisting in the concurrent isomerization of part of the maleic acid to fumaric acid. In conclusion the absorption of water in DBP and in presence of maleic anhydride/acid does not depend only from the temperature and the pressure; a likewise important parameter is the time in which the two components are in contact.

It is important to note that the absorbed water not only causes that part of maleic anhydride is converted to fumaric acid, i.e. a loss of product, but also it promotes the deposits of solids fumaric acid, characterized by a very limited solubility in water or in organic solvents, inside the internals of the columns, vessels, heat exchangers, pumps and pipes of the plant. Of course such solubility depends from the temperature, with lower values as lower is the temperature.

A second aspect of the art of the maleic anhydride absorption in an organic solvent, concerns the heat removal system.

The effluent from the oxidation reaction is well above 400° C. This reaction gas typically contains only a small amount of maleic anhydride, i.e. from 0.6 to 1.2 percent by volume, together with other components, mainly nitrogen and residual oxygen, a certain amount of not converted n-butane and with the oxidation by-products, including carbon monoxide and dioxide, water, acetic acid, acrylic acid and other minor impurities. Before to enter in the absorption column to recover the maleic anhydride, the reaction product gas is sent to one or more heat exchangers, with production of medium pressure steam and pre-heating of the relevant boiler feed water, preferably below 200° C., anyway above the dew point of the water produced in the oxidation reaction and contained in the fresh air used for the oxidation. Generally such temperature is within the range of 130 to 170° C.

The reaction gas in conclusion is characterized by a very high flowrate (from 20,000 to 160,000 Kg/h for a single commercial maleic anhydride reactor) and by a rather high temperature. It means the amount of the heat to be removed in the absorber to produce an efficient recovery of the product is very high. The heat capacity of the fresh solvent, unless to use a very huge and uneconomical amount, is not sufficient to absorb of the necessary heat load.

A third aspect not comprised in the prior art is related to the hydraulic of the internals of the absorption column.

It represents actually a typical gas/liquid contact equipment, where the volumetric ratio gas to liquid is extremely high. Who is skilled in the art of designing this type of column is familiar with the difficulties of reaching high levels of absorption efficiency.

A fourth and last aspect refers to the combination absorber/vacuum stripper. As a matter of fact the absorption solvent sent to the top of the maleic anhydride recovery column is used in a closed loop, where the maleic anhydride is removed by the enriched solvent in a reboiled column operated at very low pressure. In spite of the low pressure of this stripper and in consideration of the tendency the decomposition of the DBP at temperature higher than 200° C., it is basically impossible to completely remove the maleic anhydride from the stripped solvent such poor solvent, after adequate cooling, is recycled back to the top of the absorption tower. It means in the overhead tray of the column the gas leaving from the tray below, at this point practically without or with very low maleic content, contacts again a stream of solvent containing still maleic anhydride. It is a logical result that such maleic anhydride is partially stripped out from the solvent and it is lost in the overhead gas, typically sent to a thermal oxidizer.

As final result in the state of art, even if the removal efficiency of the absorber could be high, f.e. by using a huge number of trays of by using a huge amount of solvent, the overall recovery efficiency is always limited by the above described strip-out of product in the top tray of the absorber.

Accordingly to the above described four points, there exists a need for an improved process and apparatus for the absorption column of maleic anhydride in an organic solvent, in which the overall yield of recovery is increased and the formation of fumaric acid deposits is decreased.

SUMMARY OF THE DISCLOSURE

It is an object of the present invention to specify an improved and efficient process for recovering maleic anhydride from gaseous reaction mixture, characterized by (i) a high yields of recovery of the maleic anhydride product, (ii) a reduced formation of maleic acid and fumaric acid by-products and (iii) a reduced maintenance, thanks to the prevented formation of solid deposits in the absorption column and in other relevant equipment of the plant.

The object is achieved by a process including the following steps:
(a) Feeding the reaction gas mixture at temperature between 120 to 200° C. to an absorption column, wherein the absorber includes a feed zone, an absorption section disposed above the feed zone and a stripping section disposed below the feed zone.
(b) Recovering the maleic anhydride contained in the reaction gas in the absorption zone of an high efficiency column, consisting in: (i) a first gas cooling section where the sensible and the absorption heat is removed through the cooling of a recirculation solvent stream, withdrawn from a chimney tray located above the feed zone, cooled in an external heat exchanger by cooling water at controlled temperature and recycled back above a packing section, having low pressure drop and low liquid residence time, (ii) a second gas cooling section above the first one, having similar characteristics (recirculation of a rich solvent stream through an heat exchanger using cooling water at controlled temperature) and designed to remove from 10 to 30% of the total heat removed from the two cooling sections, (iii) a main absorption section, consisting in trays of special design, where the reaction gas at temperature below 90° C. are contacted with a stream of organic solvent stripped under vacuum, but still containing a small amount of maleic anhydride, fed under controlled conditions of flow-rate and temperature, to an intermediate tray near to the top of the absorption column, (iv) a final absorption section, consisting in one or more trays of special design, where the reaction gas, at this point containing a very small amount of maleic anhydride, are further washed by a small stream of organic solvent, typically from 10 to 25% of the total amount of the solvent, coming from the solvent washing section of the plant, where demineralized water is used to remove accumulated impurities and polymerization tars, being such solvent stream fully without, any maleic anhydride.

(c) Stripping the enriched organic solvent coming from the feed zone by a stream of hot air or hot inert gas having low humidity, in order to remove by evaporation part of the water contained in the solvent and to minimize the formation of maleic acid and particularly of fumaric acid. One of the innovation of the present invention is this stripper, which is not performed in a dedicated column, but it is integrated with the other two sections, the feed and the absorption zones. In consideration of the much lower air flow-rate compared to the reaction gas mixture sent to the feed zone, this stripping section shall have a much smaller size, therefore ensuring a lower liquid residence time and a lower conversion of maleic acid to its isomer fumaric acid. Another innovation of such dehydration stripping section consists in the use of a recycled air stream rather than fresh air, as better described under the following point (d).

(d) Stripping the small amount of maleic anhydride contained in the portion of organic solvent planned to be washed with demineralized water by a stream of hot air and reusing the air from the stripper overhead to dehydrate the rich solvent, as described in the above point (c).

Other aspects and advantages will be apparent from the following drawings, the following detailed description and the appended claims.

BRIEF DESCRIPTION OF DRAWINGS

FIG. 2 is a simplified process flow diagram of the integration between the absorber-stripper column with the water washing of the solvent to remove accumulated impurities, as described in the summary of the disclosure point (c) and (d).

FIG. 3 is a variation of the integration, where, not only the fraction of lean solvent to be water washed, but all the lean solvent from the vacuum stripper is sent to an air stripper for recovering the small amount of dissolved maleic anhydride.

DETAILED DESCRIPTION OF THE INVENTION

Figure 1:
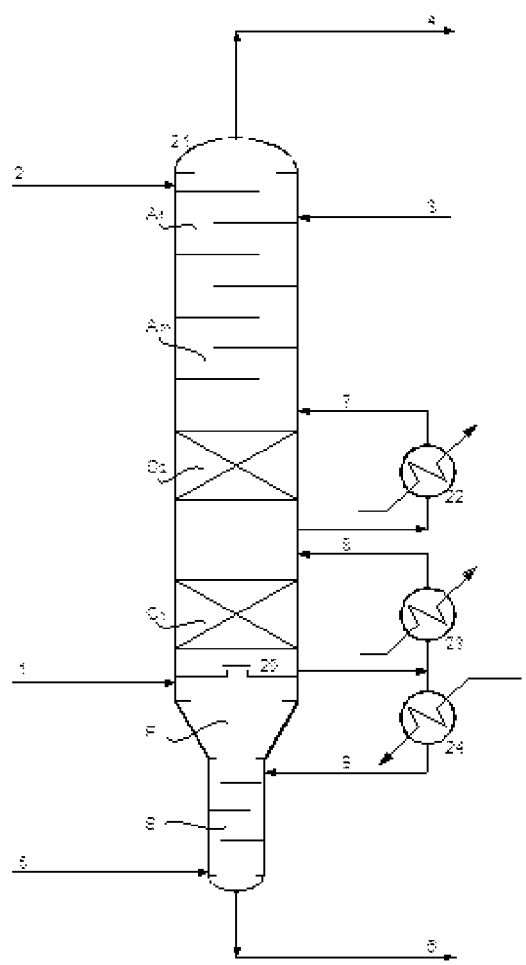
FIG. 1 is a simplified process flow diagram of the absorber-stripper column to recover the maleic anhydride from the reaction mixture, as described in the summary of the disclosure points (a), (b) and (c).

A schematic diagram of the recovery column of the maleic anhydride is shown in FIG. 1.

The cooled reaction gas 1 at a temperature between 130 to 200° C. and a pressure between 130 and 250 KPa and including maleic anhydride at a concentration from 0.6 to 1.2 percent by volume, together with other components, mainly nitrogen and residual oxygen, and with oxidation by-products, like carbon monoxide and dioxide, water, acetic acid, acrylic acid and other minor impurities, enters the feed zone "F" of the Absorption column 21 for the recovery of the maleic anhydride in liquid phase by absorption in a selective organic solvent. Selective organic solvents, such as dibutyl phthalate are widely used in the industrial applications.

Two separated and different streams of solvent are used for this purpose. A first stream 2 of very high purity solvent, with no maleic anhydride and representing 10 to 25% of the total solvent flow rate, is sent to the overhead tray of the column. In this way the strip-out of the maleic anhydride from the solvent to the overhead gas, normally sent to a thermal oxidizer or, in some cases, partially recycled to the reaction section after adequate water washing and compression, which is normal disadvantage in an absorber with a single solvent feed, is avoided or at least minimized.

One single or very few trays are used in this section "Af", characterized by a very high gas/liquid ratio.

Packing (e.g. rings, saddles etc.) or structured packing (e.g. high fractionation efficiency corrugated metal plates) are not adequate in this application to assure an efficient gas/liquid mass transfer.

Higher performances may be reached by using fractionation trays. In the group of trays, the bubble cup tray is the preferred type.

The overhead lean gas 4 from the column is substantially free of maleic anhydride and contains mainly inert gases, a small amount of not converted hydrocarbons and the oxidation by-products.

It is normally disposed to a thermal oxidized for the complete conversion of the residual hydrocarbons and of the carbon monoxide. In some cases, part of the lean gas is recycled to the reactor in order to recover the fraction of not converted n-butane. Anyway also in the use of gas recycle process, the possible presence of maleic anhydride in the recycle gas has to be considered a net loss, since the gas, to be recycled to the reactor, needs a washing operation with water, and the subsequent removal of the maleic anhydride, to protect the air compressor from corrosion risks.

It is manifest that this improvement, which is one of the aspects of this invention, may be applied with benefit both to the conventional air once-through process and to the gas recycle process.

The conditions of the lean gas are 60 to 75° C. as temperature and around 110 to 200 Kpa as pressure. Even if the low temperature promotes the recovery of the product, such temperature shall not to be considered as an independent parameter, having two limitations: (i) it cannot reach the water dew point to avoid huge condensation of water inside the column with detrimental consequences and (ii) the low temperature reduces the solubility of fumaric acid in maleic anhydride and may cause formation of solid deposits.

Below the upper absorption zone "Af", the main absorption zone, "Am" is shown in FIG. 1 as a trays column below the inlet of stream 3, which represents the main solvent stream, accounting for 75 to 90% of the total solvent flow rate. Even in this section trays are preferred over random packing or structured packing. Bubble cup trays may be used even in this section. Special design valve or sieve trays, designed for uniform liquid distribution and low residence time, are the preferred.

As above mentioned, the temperature inside the column is not a free variable. In other terms, the inlet temperature of the solvent 3 shall be strictly controlled by providing its cooling by means of cooling water at controlled temperature and by always avoiding excessive low temperatures.

Below the absorption section "Am", FIG. 1 shows two packing zones (C1 and C2) representing the cooling sections.

Starting from the feed zone "F" near to stream 1, there is a first gas cooling section "C1" where the sensible and the absorption heat is removed through the cooling of a recirculation solvent stream, withdrawn from a chimney tray located above the feed zone, cooled in an external heat exchanger 23 by cooling water at controlled temperature and recycled back (stream 8) above a packing section. In this section the temperature of the reaction gas is reduced from 130-200° C. to 70-85° C. and largely more than half of the maleic anhydride is transferred from the gas to the liquid phase. Of course a large portion of the overall heat is removed from this section. On the contrary of the upper absorption section, the liquid flow rate is dictated by the capacity of the circulation pumps. Therefore the liquid/gas ratio is much higher than in the upper part of the column. Internals having low pressure drop and low liquid residence time are used. Structured packing or metal grids with high heat transfer capacity are the preferred type.

Even in this zone it is important to minimize the liquid residence time. For the external heat exchanger 23 the use of compact plate fin or semi welded plate exchangers is preferred over the traditional shell and tube exchangers.

The same considerations are in principle valid for the second cooling section "C2" shown in FIG. 1.

Here a minor fraction of the sensible and of the absorption heat is removed through the cooling of a recirculation solvent stream, withdrawn from a chimney tray, cooled in an external heat exchanger 22 by cooling water at controlled temperature and recycled back (stream 7) above a packing section. In this section the temperature of the reaction gas is reduced to around 60-75° C. Structured packing or metal grids with high heat transfer capacity are the preferred type also in this section and, for the external heat exchanger 22, the use of compact plate fin or semi welded plate exchangers is preferred over the traditional shell and tube exchangers.

According to one embodiment of this invention, the use of a double cooling section rather than a single one, as described in the U.S. Pat. No. 3,948,623, presents two advantages: first the overall recovery efficiency is in some extent superior, second the control of the temperature profile, which is of primary importance to reach high recovery efficiency and to reduce the maintenance time and cost, results much easier. As already mentioned too high temperatures inside the absorber cause poor maleic anhydride absorption and higher isomerization rate of maleic to fumaric acid, while on the contrary too low temperatures induce the formation of solid deposits.

The last section of the column is the bottom zone "S" below the feed zone "F", where the enriched organic solvent 9, coming from the feed zone above and containing most of the maleic anhydride recovered from the reaction, gas, is stripped by a stream of hot air 5, in order to remove by evaporation part of the water absorbed in the solvent from the reaction gas and to minimize the content of maleic acid and particularly of fumaric acid in the rich solvent 6 produced from the bottom of the column 21.

Since the water stripping is enhanced by the temperature, an external heat exchanger 24, using low pressure steam as heating medium, provides to maintain the temperature at 100 to 130° C.

In another embodiment of this invention, the heating may be produced by heat recovery rather than by steam, by recovering the heat for instance from the hot lean solvent coming from the vacuum stripper.

The use of compact plate fin or semi welded plate exchangers is preferred over the traditional shell and tube exchangers, to minimize the time in which the maleic acid contained in the liquid passing through the exchanger may be converted to fumaric.

Both conventional sieve or valve trays or high efficiency structured packing may be used in this section (S). Actually the higher pressure drop of the trays compared to the packing does not affect the energy consumed by the air compressor of the reaction system, being this section below the reaction gas feed point.

The present invention introduces different innovations compared to the existing European Patent EPO459543 on the subject of the water removal from a solvent enriched in maleic anhydride.

First the water stripping is not performed in a dedicated column, but it is integrated with the other sections of the absorber; the more compact and simple configuration, together with the much smaller size of this stripping section compared to the upper cooling and absorption sections, due to the much lower air flow-rate compared to the reaction gas mixture sent to the feed zone, ensures a lower liquid residence time and therefore a lower conversion of maleic acid to its isomer fumaric acid.

With reference to the attached FIG. 2, another innovation of the dehydration stripping introduced in this invention consists in the use of a recycled air stream 10 rather than fresh air. More specifically, as shown in FIG. 2, the stream 14 represents the lean solvent coming from the vacuum stripper, where the maleic anhydride is separated from the organic solvent in a distillation column operated at sub-atmospheric pressure conditions. Such solvent still contains, due to the need to limit the temperature at the bottom of the vacuum column below the decomposition temperature of the solvent, typically dibutyl-phthalate, some limited amount, from 0.2 to 1% by weight, of maleic anhydride.

As known in the art, while most of the lean solvent, represented as stream 3, after adequate cooling at controlled temperature, may be directly recycled to the absorber 21, a certain part, represented by the stream 15, shall be subject to a water washing treatment 26, to remove the accumulated impurities and tars soluble in the aqueous stream 12 disposed to a suitable waste water treatment unit. A stream 13 of fresh water is used for the washing. Unfortunately in the prior art this water washing removes from the solvent also the above mentioned small amount of maleic anhydride, which is transformed in malic acid, representing a net loss of product and an additional organic load for the waste water treatment plant.

In the process of the present invention, the solvent stream 15, before entering the washing treatment 26, is stripped with air in a simple and relatively small size column 25 to recover the amount of maleic anhydride, which otherwise should be lost during the water washing stage.

The stripping air 5 shall have the same flowrate of that necessary to dehydrate the rich solvent at the bottom of the maleic anhydride absorber 21. The overhead vapor 10 from the stripper, consisting mainly in air with some small amount of maleic anhydride and organic solvent; is then sent to the bottom of the maleic anhydride absorber, where both the entrained organic compounds are recovered in the rich solvent. This innovative solution permits to use the same amount of stripping air in two services in series, the first to recover maleic anhydride from the lean solvent, the second to remove water from the rich solvent, reducing in this way the cost associated to the compression of this stream of air.

To enhance the maleic anhydride recovery, the stripper 25 is operated at high temperature, feeding the column by lean solvent directly from the vacuum stripper, operated at 180 to 200° C.

The enriched air 10 coming out from the top of the stripper 25 is at a temperature approaching the inlet temperature of the lean solvent 15, avoiding therefore the need of a dedicated heat exchanger to increase the temperature of the air used to dehydrate the rich solvent.

Of course also the bottom stream 11 from the stripper 25 is at rather high temperature and hence, before to enter the water washing section 26, it shall be cooled in a dedicated exchanger, not shown in the simplified scheme of FIG. 2.

FIG. 3 finally shows a variation of the process above described, where the whole lean solvent 14 from the vacuum stripper is fed to the air stripper 25. From here the bottom stream, 16 is then divided in two parts, the stream 3 recycled to the absorber 21 and the stream sent to the water washing section 26. The improvement consists in a still enhanced overall recovery of maleic anhydride thanks to a slightly reduction of the amount of maleic anhydride lost in the overhead stream 4 from the absorption column 21.

The invention is illustrated in great detail by the examples below, that anyway shall not be construed as a limitation of the scope of the invention itself or of the manner in which it may be practiced.

EXAMPLES

In a 20,000 MT/Y maleic anhydride manufacturing plant, a stream of vaporized high purity n-butane is mixed with a stream of compressed air and enters tubular reactor with around 18000 vertical tubes including a VPO catalyst type SynDane 3100 manufactured by Scientific Design Company Inc.

The reaction operates under condition of partial gas recycle from the overhead of the maleic anhydride absorption column to the suction of the air compressor, with recovery of a fraction of the n-butane not converted inside the tubes of the reactor. The effluent gas from the reactor at around 400° C., after adequate cooling in two heat exchangers in series, is fed to the recovery section of the plant under the condition shown in Table I.

TABLE I

| Reference reactor effluent | |
|---|---|
| Flow-rate, Kg/hr | 79000 |
| Composition, % mol | |
| nitrogen | 74.9 |
| oxygen | 14.3 |
| water | 7.8 |
| carbon monoxide | 0.9 |
| carbon dioxide | 0.84 |
| n-butane | 0.3 |
| maleic anhydride | 0.94 |
| acetic acid | 0.01 |
| acrylic acid | 0.01 |
| Temperature, ° C. | 170 |
| Pressure, KPa g | 0.6 |

The following examples relevant to demonstrate the maleic anhydride recovery with an organic solvent, specifically dibutyl phthalate, are the results of computer simulations using a model set-up and tested through experimental tests in pilot and in industrial plants.

Comparative Examples 1 to 6

The effluent from the reaction enters a simple absorption column with 12 theoretical trays below the bottom tray. The top tray if fed by lean dibutyl phthalate coming from the vacuum stripper after an adequate cooling.

At the solvent flow rate normally used in an efficient process as described in this invention, i.e. corresponding to a maleic anhydride concentration in the rich solvent between 10 to 20 wt %, the absorber is demonstrated to be very inefficient, due to lack of cooling. Therefore other runs have been produced with increased solvent rates, still with no column cooling. The relevant results are shown in Table II.

TABLE II

| | No cooling absorber | | | | | |
|---|---|---|---|---|---|---|
| | Ex. 1 | Ex. 2 | Ex. 3 | Ex. 4 | Ex. 5 | Ex. 6 |
| Solvent flowrate, Kg/hr | 15000 | 30000 | 40000 | 50000 | 60000 | 70000 |
| Absorber temp. profile, ° C. | | | | | | |
| top | 130 | 107 | 102 | 95 | 85 | 73 |
| bottom | 160 | 155 | 146 | 141 | 140 | 138 |
| % of MAN absorbed | 8.8 | 9.3 | 45.5 | 73.7 | 94.5 | 99.6 |
| % of water absorbed | 0.6 | 1.1 | 1.7 | 2.4 | 2.9 | 3.4 |

From the above data it is clear that, without any cooling of the absorption column and with using a reasonable amount of solvent, that is not more than 10 times the amount of maleic anhydride (MAN) present in the reaction gas, the efficiency of the system are extremely low. To reach absorption efficiency higher than 90%, the amount of solvent shall be substantially increased, at least up to more than 50 times the amount of the MAN fed to the system. The use of a so huge amount of solvent circulation has two evident disadvantages:
  high energy costs, due both to the pumping energy to circulate the solvent and particularly to the heating energy necessary for increasing its temperature to the condition of the stripping under vacuum to separate the MAN from the solvent the amount of water absorbed by the solvent increases more than proportionally than the solvent flowrate: it means that also the amount of MAN hydrated to maleic acid and to fumaric acid inside the absorber and the other equipment and pipes of the system, increases dramatically, so reducing the net yield of recovery and increasing the maintenance works.

Example 7

The absorption column has been supplied with a single cooling system. The absorption section has still theoretical trays, with further two trays at the bottom for water stripping by fresh hot air. The solvent flow rate is 15000 Kg/hr, same of example 1.

According to this invention, the lean solvent is divided in two parts: about 15% of total, without any maleic anhydride, is fed to the top tray, while the remaining 85%, containing less than 1 wt % of maleic anhydride, is fed to the second tray from the top.

TABLE II

| Single cooling absorber | |
|---|---|
| Solvent flow rate, Kg/hr | 15000 |
| Absorber temperature profile, ° C. | |
| top | 79 |
| feed zone | 86 |
| bottom | 129 |
| Heat removed, MW | 2.9 |
| % of MAN absorbed | 99.1 |
| % of water absorbed | 0.9 |

Inventive Example 8

The absorption column has been supplied with a double cooling system, according to the preferred embodiment of this invention. The absorption section has still 12 theoretical trays, with further two trays at the bottom for water stripping by fresh hot air. Also the lean solvent distribution is the same described in example 7. The solvent flow rate is 15000 Kg/hr, same of example 1 and example 7.

TABLE III

| Double cooling absorber | |
|---|---|
| Solvent flow rate, Kg/hr | 15000 |
| Absorber temperature profile, ° C. | |
| top | 68 |
| feed zone | 86 |
| bottom | 128 |
| Heat removed (total), MW | 2.9 |
| % of MAN absorbed | 99.8 |
| % of water absorbed | 0.9 |

This example 8 shows that, under the inventive conditions of the double cooling system, even if the total heat removed from the column is the same of the single cooling as shown in example 7, the efficiency in MAN absorption is increased from 99.1% to 99.8%.

Inventive Example 9

The absorption column has been supplied with a double cooling system. The absorption section has still 12 theoretical trays, with further two trays at the bottom for water stripping by hot air. Also the lean solvent distribution is the same described in example 7. The solvent flow rate is 15000 Kg/hr, same of examples 1, example 7 and example 8.

The example 9 represents the variation of the process described in FIG. 3, where the dehydration Stripping uses a recycled air stream rather than fresh air, coming from the top of an air stripper, where the whole lean solvent from the vacuum stripper is feed to the top tray to recover the maleic anhydride here contained.

TABLE IV

| Double cooling absorber and use of recycled stripping air | |
|---|---|
| Solvent flow rate, Kg/hr | 15000 |
| Absorber temperature profile, ° C. | |
| top | 68 |
| feed zone | 86 |
| bottom | 133 |
| Heat removed (total), MW | 3.2 |
| % of MAN absorbed | 99.9 |
| % of water absorbed | 0.7 |

This example 9 shows that, under the inventive conditions of the double cooling system together with the stripping of the maleic anhydride contained in the lean solvent and the double use of the stripping air as shown in FIG. 3, not only the efficiency in MAN absorption is increased to 99.9%, but even the water absorbed in the solved is reduced (the ratio amount of water absorbed in the solvent/amount of water in the gas feed is 0.007), with lower formation of maleic and fumaric acid.

The invention claimed is:

1. A process for recovering maleic anhydride from a gaseous reaction mixture, said process comprising the following steps:
   (a) feeding the gaseous reaction mixture at a temperature between 120 to 200° C. to an high efficiency absorption column, wherein the absorption column includes a feed zone, an absorption section disposed above the feed zone and a stripping section disposed below the feed zone;
   (b) recovering the maleic anhydride contained in the reaction gas in the absorption zone of said column, by:
      (i) a first gas cooling section comprising a packing section where a sensible and an absorption heat is removed through cooling of a recirculation solvent stream, withdrawn from a chimney tray located above the feed zone, cooled in an external heat exchanger by cooling water at a controlled temperature and recycled back above said packing section;
      (ii) a second gas cooling section above the first one, for removing from 10 to 30% of a total heat removed from the two cooling sections, through a recirculation solvent stream cooled in a heat exchanger using cooling water at controlled temperature;
      (iii) a main absorption section, formed from fractionation trays, where the reaction gas at a temperature below 90° C. is contacted with a stream of organic solvent stripped under vacuum, but still containing a small amount of maleic anhydride, fed under controlled conditions of flow-rate and temperature, to an intermediate tray near to the top of the absorption column,
      (iv) a final absorption section, formed from one or more suitable trays, where the reaction gas, at this point containing a very small amount of maleic anhydride, is further washed by a small stream of organic solvent, from 10 to 25% of the total amount of the solvent, coming from a solvent washing section, where demineralized water is used to remove accumulated impurities and polymerization tars, being such solvent stream fully without any maleic anhydride; and (c) stripping the enriched organic solvent coming from the feed zone by a stream of hot air in the bottom section, containing trays or packing, of the same absorption column.

2. The process according to claim 1, wherein the stream of hot air used to stripping water from the enriched solvent coming from the feed zone comprises, rather than in fresh air, in a recycled air stream coming from the overhead of a stripping column, where the small amount of maleic anhydride contained in the portion of organic solvent, assigned to be washed with demineralized water for impurities cleaning purposes, is stripped out by a stream of fresh hot air.

3. The process according to claim 1, wherein the stream of hot air used to stripping water from the enriched solvent coming from the feed zone consists in a recycled air stream coming from the overhead of a stripping column, where the small amount of maleic anhydride contained in the whole lean organic solvent, produced from the bottom of a vacuum stripper where the maleic anhydride contained in the rich solvent from the absorption column is separated by distillation, is stripped out by a stream of fresh hot air.

4. The process according to claim 1, wherein the gaseous reaction mixture is produced by using n-butane or benzene as feedstock of the partial oxidation reactor.

5. The process according to claim 1, wherein the partial oxidation reaction is produced in a tubular fixed bed reactor or in a fluidized bed reactor.

6. The process according to claim 1, wherein the oxidation reaction is produced using (i) fresh air or (ii) a mixture of fresh air and of partially exhausted air recycled back from the maleic anhydride absorber overhead or (iii) a mixture of fresh air, of partially exhausted air recycled back from the maleic anhydride absorber overhead and of high purity oxygen.

7. The process according to claim 1, wherein the organic liquid solvent used to absorbing the maleic anhydride is a dialkyl ester of phthalic anhydride or of therephthalic acid or isophthalic acid or of tetrahydrophthalic anhydride or of hexahydrophthalic anhydride.

8. The process according to claim 7, wherein the organic liquid solvent used to absorbing the maleic anhydride is dibutyl phthalate.

9. The process according to claim 8, wherein the concentration of maleic anhydride in the rich solvent at the bottom of the absorption column is in the range between 8 to 24% by weight.

10. The process according to one claim 1, wherein both the first and the second cooling sections of the maleic anhydride absorption column contain structured packing or metal grids.

11. The process according to one claim 1, wherein the trays used in the main absorption section are stepped trays or trays with other special liquid distributors, in order to obtain a low liquid load together with high separation efficiency.

12. The process according to one claim 1, wherein the trays used in the overhead absorption section are bubble cup trays in order to obtain a very low liquid load and high separation efficiency.

13. The process according to one claim 1, wherein the heat exchangers used for cooling, heating and heat recovery purposes are compact plate fin or semi welded plate exchangers, to minimize the time in which the maleic acid contained in the liquid passing through the exchanger may be converted by thermal isomerization to fumaric acid.

14. The process according to one claim 1, wherein the enriched organic solvent from the feed zone of the absorption column, before to enter the stripping section, is preheated by recovering heat from the hot lean solvent produced at the bottom of vacuum stripper, where the maleic anhydride contained in the rich solvent from the absorption column is separated by distillation.

15. The process according to one claim 1, wherein an inert gas having low humidity is used as stripping medium in place of air.

16. The process according to claim 2, wherein the gaseous reaction mixture is produced by using n-butane or benzene as feedstock of the partial oxidation reactor.

17. The process according to claim 2, wherein the partial oxidation reaction is produced in a tubular fixed bed reactor or in a fluidized bed reactor.

18. The process according to claim 2, wherein the oxidation reaction is produced using (i) fresh air or (ii) a mixture of fresh air and of partially exhausted air recycled back from the maleic anhydride absorber overhead or (iii) a mixture of fresh air, of partially exhausted air recycled back from the maleic anhydride absorber overhead and of high purity oxygen.

19. The process according to claim 2, wherein the organic liquid solvent used to absorbing the maleic anhydride is a dialkyl ester of phthalic anhydride or of therephthalic acid or isophthalic acid or of tetrahydrophthalic anhydride or of hexahydrophthalic anhydride.

20. The process according to one claim 2, wherein the heat exchangers used for cooling, heating and heat recovery purposes are compact plate fin or semi welded plate exchangers, to minimize the time in which the maleic acid contained in the liquid passing through the exchanger may be converted by thermal isomerization to fumaric acid.

* * * * *